United States Patent [19]

Burke et al.

[11] Patent Number: 4,803,290
[45] Date of Patent: Feb. 7, 1989

[54] NONANOL/NONENE ANTIMICROBIAL COMPOSITIONS

[75] Inventors: Basil A. Burke, Palo Alto, Calif.; Muraleedharan Nair, East Lansing, Mich.

[73] Assignee: PCRI, Inc., Dublin, Calif.

[21] Appl. No.: 55,645

[22] Filed: May 29, 1987

[51] Int. Cl.$^4$ .................. A01N 43/30; C07D 317/50; C07D 317/54

[52] U.S. Cl. .................................. 514/464; 514/465; 549/434; 549/445

[58] Field of Search ................ 514/464, 465; 549/445, 549/434

[56] References Cited

U.S. PATENT DOCUMENTS 3,812,262  5/1974  Chodnekar et al. ............ 514/464 X
3,878,200  4/1975  Diana et al. .................... 549/445 X
3,923,832 12/1975  Leopold ........................... 549/445 X

FOREIGN PATENT DOCUMENTS 128129 of 1970 India.

OTHER PUBLICATIONS

Devakumar et al., "New Sesamol Ethers as Pyrethrum Synergists" in *Agric. Biol. Chem.*, 49, pp. 725-730 (1985).
Homans et al., "Direct Bioautography on Thin-layer chromatograms as a Method for Detecting Fungitoxic Substances" in *J. Chromatog*, 51, pp. 327-329 (1970).
Dallacker, "Zur Synthese von Dimethoxy-methylendioxy-allylbenzden" in *Chem. Ber*, 102, pp. 26663-2676 (1969).
Burke et al., "Phenylpropene, Benzoic Acid and Flavanoid Derivatives from Fruits of Jamaican Piper Species" in *Phytochem.*, 25, pp. 1427-1430 (1986).
Nair, Thesis, "Chemical and Preliminary Biological Investigation of Some Jamaican Medicinal Plants", University of West Indies (1984).

*Primary Examiner*—Johnnie R. Brown
*Assistant Examiner*—W. Catchpole
*Attorney, Agent, or Firm*—Jacques M. Dulin

[57] ABSTRACT

Substituted 5'-nonanol/5'-nonene compounds which exhibit important antimicrobial and antifungal activity, compositions and methods of delivery against pathovars and pathogens, and methods of synthesis from commonly available reactants. The antimicrobial composition active ingredient is one or more substituted 1,2-alkylidenedioxybenzene compounds of the formula:

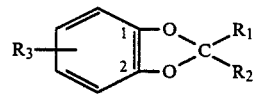

where $R_3$ is selected from 5'-nonanol and 5'-nonene, and $R_1$ and $R_2$ are selected from H and $C_1$–$C_5$ alkyl, alkenyl and alkynyl groups. The preferred compounds are 5-(5'-hydroxy-5'-nonanyl)-1,1-methylenedioxybenzene and 4-(5'-non-4'-enyl)-1,2-methylenedioxybenzene. Compositions including these compounds exhibit antimicrobial activity against a variety of pathogens and pathovars, e.g., *Xanthomonas campestris* spp. bacteria, antifungal activity against a variety of fungi and bacteria, and are highly specific, e.g., having antifungal activity against wheat powdery mildew and cucumber downy mildew, but do not affect seed germination or have appreciable herbicidal or insecticidal activity. Methods and compositions for delivery of these agents against such pathogens, and methods of chemical synthesis of the compounds are disclosed.

16 Claims, No Drawings

NONANOL/NONENE ANTIMICROBIAL COMPOSITIONS

FIELD

This application relates to substituted nonane/nonene compounds which exhibit important antimicrobial (anti bacterial and antifungal) activity, compositions and methods of delivery against pathogens, and methods of synthesis from commonly available reactants.

More particularly, this application relates to substituted 1,2-alkylidene compounds of the formula:

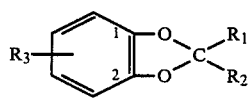

Formula I where $R_3$ is selected from 5'-nonanol (5'-hydroxy-5'-nonanyl) and 5'-nonene (5'-non-4'-enyl) and $R_1$ and $R_2$ are selected from H and $C_1$–$C_5$ alkyl, alkenyl and alkynyl groups. The preferred compounds are 4-(5'-hydroxy-5'-nonanyl)-1,2-methylenedioxybenzene, and 4-(5'-non-4'-enyl)-1,2-methylenedioxybenzene. These compounds exhibit antimicrobial activity against a variety of pathogens and pathovars, e.g., *Xanthomonas campestris* spp. bacteria, antifungal activity against a variety of fungi and bacteria, and are highly specific, e.g., having antifungal activity against wheat powdery mildew and cucumber downy mildew but do not affect seed germination or have appreciable herbicidal or insecticidal activity in wheat. The invention is also directed to methods and compositions for delivery of these compounds against such pathogens and to methods of chemical synthesis of the compounds.

BACKGROUND

Dallacker [1] reports the synthesis of dimethoxy-methylene-dioxy-allylbenzenes including pseudo-dillapiole (Dallacker's pseudo-dillapiole compound 8f, 4,5-dimethoxy-2,3-methylenedioxy-1-allyl-benzene) and nor pseudo-dillapiole (Dallacker's compound 8e, 6-methoxy-2,3-methylenedioxy-4-allyl-phenol). Dallacker also shows a number of position isomers of those allyl benzenes, including dillapiole (Dallacker's "Dill Apiole", 2,3-Dimethoxy-4,5-methylenedioxy-allyl-benzene), apiole (Dallacker's compound 7, 5,6-dimethoxy-2,3-methylenedioxyallyl-benzene), 2,5-dimethoxy-3,4-methylenedioxy-allyl-benzene (Dallacker's "Petersilen-Apiol"), 4,6-dimethoxy-2,3-methylene-dioxy-allyl-benzene (Dallacker's compund 4i),and 2,6-dimethoxy-3,4-methylenedioxy-allyl-benzene (Dallacker's compound 5i). Dallacker also shows monomethoxy, allyloxy, hydroxy (allyl-phenol), nitro, amino, acetamino, and propenyl derivatives.

However, these compounds of Dallacker are very dissimilar to Applicants' compounds, and he does not teach or suggest nonane/nonene substituted alkylidenedioxybenzene compounds. Further, Dallacker neither shows nor suggests any biological activity, much less antimicrobial or antifungal properties.

Several methylenedioxyphenyl compounds and the compound dillapiole 5,6-dimethoxy-3,4-methylenedioxy-1-allyl benzene, were reported by Devakumar, et al. [2], and in an Indian patent [3], No. 128,129 (1969) to have synergic activity with pyrethrum insecticides.

In the provisional specification of the Indian Pat. No. 128,129 attention was focused on the propyl analog of dillapiole because of undesirable physiological side effects of the allyl side chain. The allyl side chain was hydrogenated in the presence of a Raney-nickel catalyst, and the resulting dihydro compound was found to be an effective synergist with pyrethrins against houseflies, cockroaches and flour beetles.

Citrus Canker is a deadly plant disease caused by *Xanthomonas campestris* spp. This disease causes millions of dollars damage to citrus crops in the world each year, adversely affecting the world food supply. Currently, the only solution is containment by isolation/removal of the diseased plants, followed by burning the groves. A recent newspaper article (S. F. Chronicle Feb. 18, 1986, p. 17) reports that a serum of "old beer and bacteria" developed by RAM Chemical of Borger TX said to be 100% effective in stopping outbreaks of canker.

Wheat powdery mildew (WPM) is a fungal pathovar, *Erysiphe graminis*, that causes extensive damage to wheat crops. A variety of compounds are used to combat these diseases. For example, wheat is treated with duPont's BENOMYL, methyl 1-(butylcarbamoyl)-2-benzimidazolecarbonate, Farbenfabriken Bayer's EDIFENPHOS, O-ethyl-S,S-diphenyl-dithiophosphate, and Bayer AG/Mobay Chemical Company's BAYLETON, 1-(4-chlorophenoxy)-3,3-dimethyl-1-(1H-1,2,4-triazol-1-1)-2-butanone. However, the Edifenphos can not be sold or used in the U.S., is toxic to fish, should not be mixed with alkaline materials, and cannot be used within 10 days before or after a propanil application. Benomyl is likewise toxic to fish, livestock may not be grazed on treated areas, it should not become wet during storage or combined with alkaline pesticides and apples do not express fine fruit finish. Bayleton exhibits some plant stunting and deformation on ornamentals when used at excessive rates and is toxic to fish.

There is thus a need for new compounds which are effective against such plant diseases.

THE INVENTION

Objects

It is among the objects of the invention to provide a new class of compounds having antimicrobial properties, more specifically antifungal and antibacterial properties.

It is another object of the invention to provide substituted nonane/nonene compounds which have antibacterial and/or antifungal properties.

It is another object of the invention to provide compositions and methods of delivery of the compounds of this invention to combat bacterial and fungal pathogens and pathovars, more particularly species of *Xanthomonas campestris* and *Erysiphe graminis*.

It is another object of this invention to provide methods of synthesizing the compounds of this invention.

Still other objects will be evident from the summary, detailed description and claims.

SUMMARY

We have discovered that substituted 1,2-alkylidenedioxybenzene compounds exhibit important antimicrobial and antifungal activity. More specifically the class of compounds is represented by the formula:

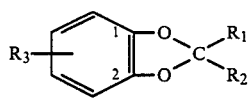

Formula I where $R_3$ is selected from 5'-nonanol (5'-hydroxy-5'-nonanyl) and 5'-nonene (5'-non-4'-enyl) and $R_1$ and $R_2$ are selected from H and $C_1$–$C_5$ alkyl , alkenyl and alkynyl groups. The preferred compounds are 4-(5'-hydroxy-5'-nonanyl)-1,2-methylenedioxybenzenes and 4-(5'-non-4'-enyl)-1,2-methylenedioxybenzenes. These compounds exhibit antimicrobial activity against a variety of pathogens and pathovars, e.g., *Xanthomonas campestris pv. carotae* and *pv. campestris,* pathovars which are closely related to the bacteria *Xanthomonas campestris pv. citrii* the causative agent of citrus canker. The compounds also show antifungal activity against a variety of fungi and bacteria, and are highly specific, e.g., having antifungal activity against wheat powdery mildew and cucumber downy mildew but do not affect seed germination, or have appreciable herbicidal or insecticidal activity. The invention is also directed to methods and compositions for delivery of these compounds against such pathogens and to methods of chemical synthesis of the compounds.

More particularly, the 5'-nonanol (5'-hydroxy-5'-nonanyl) compound ($R_3$=5'-nonanol, R, and $R_2$=H) was found to have high activity for preventing infection of wheat by *Erysiphe graminis,* the pathogen responsible for wheat powdery mildew (herein WPM), on the order of 95% at 100 ppm compared to the following reference compounds: 0% for Rohm & Haas's MANCOZEB, (16% Mn, 2% Zn and 62% ethylenebisdithiocarbamate ion/Mn ethylenebisdithiocarbamate plus Zn ion) at up to 300 ppm; 100% for du Pont's BENOMYL in the range of 38–300 ppm; 100% for Farbenfabriken Bayer's EDIFENPHOS in the range of 75–300 ppm; 100% for Nachricten Bayer's BAYLETON in the range of 38–100 ppm; and 0% for both Nihon Nohyaku's FUJI-ONE, (diisopropyl-1,3-dithiolan-2-ylidane malonate), and Meji Sechakaisha's ORYZEMATE, (3-allyloxy-1,2 benzoisothiazole-1,1-dioxide) at up to 300 ppm.

The 5'-nonanol (5'-hydroxynonane) compound was also found to be highly specific, being substantially ineffective against: *Pseudoperonospora cubensis* the pathogen of cucumber downy mildew; *Piricularia oryzae,* the pathogen of rice blast; *Pellicularia filamentosa,* the pathogen of rice sheath blight; *Phytophtora infestans,* the pathogen of tomato leaf blight; and *Puccinia recondita,* the pathogen of wheat leaf rust.

At $ED_{50}$ concentrations on the order of 10 ppm this compound was also effective against *Xanthomonas campestris pv. carotae* and *pv. campestris* pathovars which are closely related to the bacteria *Xanthomonas campestris pv. citrii,* the causative agent of citrus canker disease.

The 5'-nonene (5'-non-4'-enyl) compound ($R_3$=5'-nonene, $R_1$ and $R_2$=H) is effective and equally highly specific against WPM (*Erysiphe graminis*) and *Pseudoperonospora cubensis,* the pathogen responsible for cucumber downy mildew (CDM) on the order of 50% at 100 ppm compared to the same reference compounds. In contrast the 5'-nonanol (5'-hydroxynonane) compound is ineffective against CDM, but both are effective on *Xanthomonas campestris* spp.

Further evidence of specificity is shown by the fact that neither compound alone proved effective as an herbicide or as an insecticide. For example, the 5'-nonanol compound was ineffective against: pigweed, average monocots, green foxtail, signal grass, southern armyworm, mexican bean beetle, cucumber phytotoxicity, southern corn rootworm, green peach aphid, two-spotted spider mite, and southern root knot nematode, and only slightly effective against average dicots (11%) and velvet leaf (21%) in post emergent application at 4 lbs/acre. The 5'-nonene compound was ineffective against: all the above weeds for the 5'-nonanol compound, and in addition showed no activity againt average dicots and velvet leaf.

These compounds are also active in the range of as low as about 10–30 ppm against a range of fungi, e.g., *Cladosporium herbarum,* a saprophyte, and against *Helminthosporium carbonum, Alternaria brassicicola, Pyrenochaeta terrestris,* and *Alternaria chrysanthemi,* the pathogens of maize, cabbage, onions and chrysanthemum, respectively. In contrast they were relatively ineffective at reasonable concentration levels against *Agrobacterium tumefaciens, Rhizobium japonicum* and certain yeast.

The compounds are sufficiently volatile to be applicable to plants as an aerosol. Thus, they also meet the need for a relatively short effective lifetime on crops. The preferred application is foliar, employing a suitable carrier fluid in the range of 5–500 ppm, and pre-infection application is preferred.

The compounds are synthesized from piperonylic acid methyl ester in THF with butyl lithium to produce the 5'nonanol (5'-hydroxynonane) derivative. Therafter the 5'-nonene compound is produced from the 5'-nonanol intermediate by heating, vacuum distillation or drying over $SiO_2$.

DETAILED DESCRIPTION OF THE BEST MODE OF CARRYING OUT THE INVENTION

The following detailed description is by way of example and not by way of limitation of the principles of this invention and has reference to the specific examples below.

Example 1-Synthesis of 5'-Nonanol Compound ($R_3$=5'-hydroxy-5-nonanyl, $R_1$ and $R_2$=H) and the 5'-Nonene Compound ($R_3$=5'-non-4'-enyl; $R_1$ and $R_2$=H)

UV spectra were recorded with a Perkin Elmer Lambda 5 Spectro-photometer, IR Spectra was recorded on Perkin-Elmer 1420 spectrophotometer, $^1H$-NMR and $^{13}C$-NMR on Varian XL-300 and the high resolution mass spectra on VG analytical 7070E-HF.

The synthesis route for the compounds is as follows:

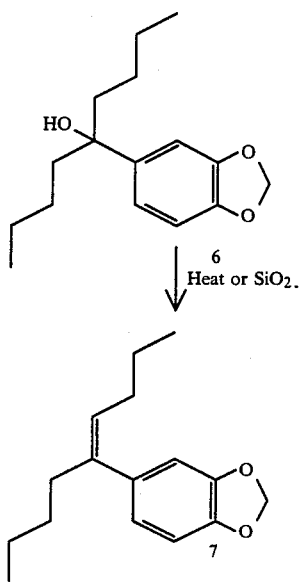

4-(5'-hydroxy-5'-nonanyl)-1,2-methylenedioxybenzene (Compound 6):

Piperonylic acid methyl ester (40 g) in THF (250 ml) was reacted at −10° C. under argon gas with butyl lithium in hexane (100 ml, 1.1 mole) for 2½ hours. The reaction mixture was diluted with crushed ice and brine and extracted with ethyl acetate. The removal of ethyl acetate gave a dark yellow liquid which was further purified by reactivated silica column using hexane as the eluant. The product was a colourless viscous liquid (50 g);

IR $\nu max_{liq\,film} cm^{-1}$: 1610, 3550;

UV $\lambda max_{MeOH} nm$ ($\epsilon$): 223 (8133), 256 (7512), $^1$H-NMR $\delta$ (CDCl$_3$); 0.87 (6H, t, J=3 Hz, CH$_3\times$2), 1.25 (8H, m, CH$_2\times$4), 1.66 (4H, t, J=3 Hz, CH$_2\times$2), 5.94 (2H, s, OCH$_2$O), 6.86 (1H, d, J=6 Hz, C-5), 6.80 (1H, d, J=2 Hz, C-2), 6.77 (1H, d, J=6 Hz, C-6);

$^{13}$CNMR ppm (CDCl$_3$); 14.02 (q, 2$\times$CH$_3$), 23.09, 25.62, 42.84 (all t, CH$_2$), 100.79 (t, OCH$_2$O) 100.28, 118.31$\times$2 (all d), 77.4 (S, Ar-C-O), 107.59, 140.83, 145.72, 147.48 (all s);

HRMS m/z: 264.1699 (M$^+$, 5, C$_{16}$H$_{24}$O$_3$), 246.1602 (M$^+$-H$_2$O, 100, C$_{16}$H$_{22}$O$_2$), 247.1698 (M$^+$-OH, 22, C$_{16}$H$_{23}$O$_2$).

4-(5'-non-4'-enyl)-1,2-methylenedioxybenzene (Compound 7):

Compound (6) on heating converted to (7). An attempted vacuum distillation of (6) at 145°–146° C./0.3 mm of Hg produced only compound (7). The alkene is a colourless liquid.

IR $\nu max_{liq\,film}$ 1610, 2900;

UV $\lambda max_{MeOH} nm(\epsilon)$: 212 (7889), 223 (8245), 256 (7303), 294 (4408);

$^1$H-NMR $\delta$(CDCl$_3$): 0.84 (3H, t, J=3 Hz, CH$_3$), 0.94 (3H, t, J=3 Hz, CH$_3$), 1.29 (6H, m, CH$_2\times$3), 2.16 (2H, q, J=6 Hz, CH$_2$), 2.40 (2H, m, CH$_2$), 5.92 (2H, s, OCH$_2$O), 6.78 (1H, m, C=CH), 6.87 (1H, d, J=6 Hz, C-5), 6.80 (1H, d, J=2 Hz, C-2), 6.75 (1H, d, J=6 Hz, C-6);

$^{13}$C NMR ppm (CDCl$_3$): 14.0 (q, CH$_3\times$2), 22.66 (t, CH$_2$), 23.33 (t, CH$_2$), 30.00 (t, CH$_2$), 30.6, (t, CH$_2$), 31.33 (t, CH$_2$), 100.60 (t, OCH$_2$O), 107.30(d), 108.31(d), 119.6(d), 128.33(d), 138.33(s), 140.00(s), 146.33(s), 148.00(s);

HRMS m/z: 246.1619 (M$^+$, 100, C$_{16}$H$_{22}$O$_2$).

EXAMPLES 2–12 Determination of Biological Activity

In the following examples, the 5'-Nonanol/5'-nonene compounds were tested at various concentrations for the ED$_{50}$ level by the dilution method in nutrient agar or suspension medium. The test organisms were: The fungi *Cladosporium herbarum* (herein CH), *Helminthosporium carbonum* (HC), *Alternaria brassicicola* (AB), *Pyrenochaeta terrestris* (PT), and *Alternaria crysanthemi* (AC); bacteria *Xanthomonas campestris* PV. campestris (XC campestris), *Xanthomonas campestris* pv. carotae (XC carotae), *Agrobacterium tumefaciens* (AT), *Rhizobium japonicum* (RJ); and yeast *Saccharomyces cerevisiae* from Universal Foods (yeast I), and a haploid lab strain from Yeast I (Yeast II).

For *Xanthomonas campestris* bacteria, the enriched nutrient medium (ENM) used was made by mixing 0.5% glucose and 1.5% commercial nutrient agar. The Wantanabe broth used for bacterial suspension was made up with 0.1% L-glutamic acid, 0.05% L-methionine, 0.3% (NH$_4$)$_2$HPO$_4$, 0.2% KH$_2$PO$_4$, 0.1% MgCl$_2$.6H$_2$O, 0.0001% FeSO$_4$.7H$_2$O, 0.000075% MnSO$_4$.H$_2$O and 0.5% sucrose, and the pH was adjusted to 6.5–7.0. The *Agrobacterium tumesfaciens* was assayed in Luria-Bertani (LB) medium containing trylone 1%, yeast extract 0.5%, NaCl 1% and NaOH. 0.1%. *Rhizobium japonicum* was assayed in yeast-mannitolmedium containing 0.05% NaCl, 0.01% yeast extract, 0.02% K$_2$HPO$_4$, 1% Mannitol and 0.2% concentrated salt solution (the concentrated salts were 0.1 g MgSO$_4$.7H$_2$O, 0.02 g FeCl$_3$, 0.04 g CaCl$_2$, 0.83 ml HCl and 99.0 ml H$_2$O), and the pH was adjusted to 7.2. The medium for yeast contained yeast extract 1%, bactopeptone 2%, adenine (1 mg/ml) 25% by vol., uracil (1 mg/ml) 2% by vol, agar 2%, and glucose (50%) 4% by vol. The V-8 medium for fungi consisted of V-8 juice (200 ml), CaCO$_3$ (3.0 g) and agar (15.0 g) per 1000 ml medium, and the pH adjusted to 7.2. All the cultures were incubated at 27 for 3–7 days.

Determination of ED$_{50}$ in fungi:

ED$_{50}$ values for the fungi were calculated by determining inhibition of mycelial growth on solid nutrient medium (V-8 juice agar). A small plug of the desired fungus on solid nutrient agar, was placed on solid nutrient agar previously incorporated with the compounds under investigation. The concentrations used were from 5 ppm to 100 ppm. The inhibition of the mycelial growth was recorded at the end of 72 hrs.

Determination of ED$_{50}$ on bacteria and yeast:

Bacterial and yeast bioassay were carried out in their respective liquid nutrient medium. The compound to be assayed was inoculated with the desired bacteria or yeast and was shaken on a rotary shaker at 170 ppm (28C) for two days. The samples were visually examined or by measuring the absorbance at 640 nm using a UV-visible spectrophotometer. For a bacterial solution, at 640 nm, an OD value of 0.685 indicates 129$\times$10$^4$ colony forming units (CFU). Before inoculation, each bacteria/yeast in their respective liquid nutrient-medium were diluted to approximately 10$^4$ CFU per ml. 1 ml aliquots of this clear bacterial/yeast solution were used to inoculate the various concentrations of the compound being tested, and at the end of 2 days shaking, activity was recorded by the turbidity of the solution. A clear solution indicated the inhibition. For lower concentrations of the test compounds, after the two days inoculation, aliquots were further diluted with the respective medium; 10 μl of these diluted solutions were applied on solid ENM medium and the number of colony forming units were counted.

The antimicrobial activity of compounds of this invention is represented in Tables I and II below. Prior to these determinations, a preliminary assay was carried out using *Cladosporium herbarum* on TLC plates [4]. The compounds of this invention showed total inhibition at the 5 μg level during TLC assay.

TABLE I

Antifungal activity shown as $ED_{50}$ concentration in ppm.

| | EXAMPLES | | | | |
|---|---|---|---|---|---|
| Compound | 2 CH | 3 HC | 4 AB | 5 PT | 6 AC |
| 6 = 5'-Nonanol | 15 | 9 | 8 | 20 | 20 |
| 7 = 5'-Nonene | 25 | 20 | 6 | 20 | 20 |

CH = *Cladosporium herbarum*; HC = *Helminthosporium carbonum*; AB = *Alternaria brassicicola*; PT = *Pyrenochaeta terrestris*; AC = *Alternaria chrysanthemi*

TABLE II

Antibacterial yeast activity shown as $ED_{50}$ concentration in ppm.

| | EXAMPLES | | | | | |
|---|---|---|---|---|---|---|
| Compound | 7 X.C. *campestris* | 8 X.C. *carotae* | 9 AT | 10 RJ | 11 Yeast-I | 12 Yeast-II |
| 6 = 5'-Nonanol | 20 | 20 | >200 | >500 | >500 | >500 |
| 7 = 5'-Nonene | 50 | 50 | >200 | >500 | >500 | >500 |

XC = *Xanthomonas campestris*; AT = *Agrobacterium tumefaciens*; RJ = *Rhizobium japonicum*; Yeast-1 = *Saccharomyces cerevisiae* from Universal Foods; Yeast II = haploid PCRI lab strain from Yeast-1.

DISCUSSION

Table I shows the growths of *C. herbarum* (saprophyte), *H. carbonum* (maize pathogen), *A. brassicicola* (cabbage pathogen), *P. terrestris* (onion pathogen) and *A. chrysanthemi* (chrysanthemum sp.) were inhibited by all compounds in the nutrient agar medium at low concentrations. At 50 ppm the compounds totally inhibited the growth of CH and HC. At concentrations more than 20 ppn, the compounds totally inhibited growth of all fungi assayed. The compounds showed total kill at 50 ppm.

Table II, the bacterial and yeast bioassay, showed identical activity for the compounds of the invention. The yeast were unaffected by the 500 ppm concentration level of the compounds. *A. tumefaciens* and *R. japonicum* suffered growth retardation at concentrations greater than 200 ppm. *X. campestris* pv. *campestris* (cabbage pathogen) and pv. *carotae* (carrot pathogen) were affected by low concentrations of the compounds.

Example 13-Seed Germination Bioassay

A seed germination bioassay test for the compounds was carried out using cress, lettuce, corn and soybean seed. At 250 μg/ml concentrations studied, it was evident that none of the compounds had any effect on the seed germination.

EXAMPLES 14–15 In Vivo Fungicide Screen Evaluation

A series of tests were run to screen for in vivo effectiveness of compounds of the invention. The purpose was to detect activity, and the compounds were applied on plants in greenhouse and growth chamber environments by spray on the foliage at the rate of 100 ppm before the onset of infection by the plant pathogen. The methodology is designed to establish the inter-relationship between host, pathogen and environment necessary to obtain a measure of the test compound's effectiveness. The compounds of the invention were tested in a non-persistent type test for activity as compared to standard commercial fungicides MANCOZEB, BENOMYL, EDIFENPHOS, BAYLETON, FUJI-ONE and ORYZEMATE as reference compounds (see Summary above). Table III shows the results for the 5'-nonanol compound (Example 14) and the 5'-nonene compound (Example 15):

TABLE III

In Vivo Fungicide Screening Tests
Values expressed as % compared to control at 100 ppm

| | CDM | RB | RSB | TLB | WLR | WPM |
|---|---|---|---|---|---|---|
| Example 14 5'-Nonanol (Compound 6) | 0 | 0 | 0 | 0 | 0 | 95 |
| Example 15 5'-Nonene (compound 7) | 50 | 0 | 0 | 0 | 0 | 50 |

CDM = cucumber downy mildew pathogen *Pseudoperonospora cubensis*; RB = rice blast pathogen, *Piricularia oryzae*; RSB = rice sheath blight pathogen *Pellicularia filamentosa*; TLB = tomato leaf blight pathogen *Phytophtora infestans*; and WLR = wheat leaf rust pathogen, *Puccinia recondita*.

EXAMPLE 16 Specificity

As noted above the compounds are ineffective as herbicides against one or more of the following weeds: pigweed, average monocots, green foxtail, and signal grass in both pre-emergent and post-emergent screening tests at 4 lbs/acre application rates. In addition, while neither compound 6 nor 7 is effective as a preemergent against average dicots and velvet leaf, only the 5-nonane (nonanol) compound 6 did not show some activity in the 4 lb/acre post-emergent application test: 11% for average dicots and 21% for average monocots. The 5-nonene compound showed no post emergent activity at that application level. Likewise, the compounds showed no insecticide activity, measured as effective kill rates at dosages varying between 150 to 600 ppm, against AW (southern armyworm), BB (mexican bean beetle), CPH (cucumber phytotoxicity), CRW (southern corn rootworm), GPA (green peach aphid), MTA (two-spotted spider mite), and NEM (southern root knot nematode).

Surprisingly, compounds of the invention, particularly the 5'-nonanol and 5'-nonene compounds are highly specific and selectively active. The bioassay results indicated that the compounds have no significant difference in their activities against the microorganisms studied and in not inhibiting seed germination. Activity on microbes but lack of adverse effect on plants by these compounds is a distinct advantage in their use as antimicrobial agents. The activity against varieties of *Xanthomonas campestris* bacteria indicates that the compounds of the invention may have particular utility as control agents against the dreaded citrus canker disease which is caused by the related *Xanthomonas campestris pv. citrii* bacteria.

It should be understood that various modifications within the scope of this invention can be made by one of ordinary skill in the art without departing from the spirit thereof. We therefore wish out invention to be defined by the scope of the appended claims as broadly as the prior art will permit, and in view of this specification if need be.

Citations

1. Dallacker, F., Zur Synthese von Dimethoxy-methlenedioxy allylbenzolen. Chem. Ber. 102, 2663–2676 (1969).
2. Devakumar, C., Saxena, v.s., and Mukerjee, S. K., Agri. Biol. Chem. 49(3): 725 (1985).
3. Indian Patent No. 128, 129 (1969), Improvements in or relating to methylenedioxyphenyl derivatives, Issued to The Director, Indian Agricultural Research Institute.
4. A. L. Homans and A. Fuchs, *J. Chromatog.* 51, 327 (1970).

Other Information

5. Burke, B., and Nair, M., Phenylpropene, Benzoic Acid and Flavonoid Derivatives from Fruits of Jamaican Piper Species, Phytochemistry, Vol. 25, No. 6 pp 1427–1430, June 1986.
6. Nair, M., Thesis, *Chemical and Preliminary Biological Investigations of Some Jamaican Medicinal Plants,* University of the West Indies, Mona, Kingston, Jamaica, May 1984.

We claim:

1. An antimicrobial composition comprising in operative combination:

(a) at least one substituted 1,2-alkylidenedioxybenzene compound in an antimicrobially sufficient amount in association with a carrier material for application to plants;

(b) said substituted 1,2-alkylidenedioxybenzene compound being selected from the group consisting essentially of compounds of the formula:

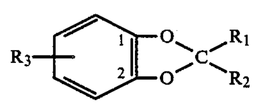

wherein $R_3$ is selected from 5'-hydroxy-5'-nonanyl and 5'-non-4'-enyl, and $R_1$ and $R_2$ are selected from H and $C_1$–$C_5$ alkyl, alkenyl and alkynyl groups.

2. An antimicrobial composition as in claim 1 wherein $R_1$ and $R_2$ are H.

3. An antimicrobial composition as in claim 2 wherein $R_3$ is 5'-hydroxy-5'-nonanyl.

4. An antimicrobial composition as in claim 2 wherein $R_3$ is 5'-non-4'-enyl.

5. An antimicrobial composition as in claim 1 wherein said carrier is a fluid.

6. An antimicrobial composition as in claim 2 wherein said carrier is a fluid.

7. An antimicrobial composition as in claim 3 wherein said carrier is a fluid.

8. An antimicrobial composition as in claim 4 wherein said carrier is a fluid.

9. A method of reducing the incidence of attack of plant fungal pathovars comprising:

(a) applying to plants before the onset of infection the composition of claim 1 at a rate of from about 50 to 250 ppm.

10. A method of reducing the incidence of attack of plant microbial pathovars comprising:

(a) applying to plants before the onset of infection the composition of claim 2 at a rate of from about 50 to 250 ppm.

11. A method of reducing the incidence of attack of plant microbial pathovars comprising:

(a) applying to plants before the onset of infection the composition of claim 3 at a rate of from about 50 to 250 ppm.

12. A method of reducing the incidence of attack of plant microbial pathovars comprising:

(a) applying to plants before the onset of infection the composition of claim 4 at a rate of from about 50 to 250 ppm.

13. A method as in claim 9 comprising foliar application in the form of a liquid carrier containing said composition.

14. A method as in claim 10 comprising foliar application in the form of a liquid carrier containing said composition.

15. A method as in claim 11 comprising foliar application in the form of a liquid carrier containing said composition.

16. A method as in claim 12 comprising foliar application in the form of a liquid carrier containing said composition.

* * * * *